(12) United States Patent
Demos et al.

(10) Patent No.: US 7,149,567 B2
(45) Date of Patent: Dec. 12, 2006

(54) NEAR-INFRARED SPECTROSCOPIC TISSUE IMAGING FOR MEDICAL APPLICATIONS

(75) Inventors: Stavros Demos, Livermore, CA (US); Michael C. Staggs, Tracy, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/293,590

(22) Filed: Dec. 2, 2005

(65) Prior Publication Data

US 2006/0142661 A1 Jun. 29, 2006

Related U.S. Application Data

(62) Division of application No. 10/190,231, filed on Jul. 5, 2002, now Pat. No. 7,016,717.

(51) Int. Cl.
*A61B 6/00* (2006.01)

(52) U.S. Cl. .................................................... 600/473

(58) Field of Classification Search ................ 600/473, 600/475, 407; 250/330, 316.1, 338.1, 472.1; 348/164
See application file for complete search history.

(56) References Cited

U.S. PATENT DOCUMENTS

| | | | |
|---|---|---|---|
| 4,930,516 A | 6/1990 | Alfano et al. | |
| 4,957,114 A | 9/1990 | Zeng et al. | |
| 5,042,494 A | 8/1991 | Alfano | |
| 5,131,398 A | 7/1992 | Alfano et al. | |
| 5,261,410 A | 11/1993 | Alfano et al. | |
| 5,348,018 A | 9/1994 | Alfano et al. | |
| 5,467,767 A | 11/1995 | Alfano et al. | |
| 5,713,364 A * | 2/1998 | DeBaryshe et al. | 600/476 |
| 5,769,081 A | 6/1998 | Alfano et al. | |
| 5,813,987 A * | 9/1998 | Modell et al. | 600/473 |
| 5,847,394 A | 12/1998 | Alfano et al. | |
| 6,954,667 B1 * | 10/2005 | Treado et al. | 600/476 |
| 6,965,793 B1 * | 11/2005 | Treado et al. | 600/476 |

OTHER PUBLICATIONS

Udagawa, M., et al., "Aberrant Porphyrin Metabolism in Hepatocellular Carcinoma," Biochemical Medicine 31, pp. 131-139, Academic Press, Inc. (1984).
Pitts, J., et al., "Autofluorescence characteristics of immortalized and carcinogen-transformed human bronchial epithelial cells," Journal of Biomedical Optics 6(1), pp. 31-40 (Jan. 2001).
Zawirska, B., "Comparative Porphyrin Content in Tumors with Contiguous Non-Neoplastic Tissues," Neoplasma 26, 2, pp. 223-229 (1979).
Malik, Z., et al., "Destruction of erythoroleukaemic cells by photoactivation of endogenous porphyrins," Health Sciences Research Center, Dept. of Life Sciences, Bar-Ilan Univeristy, Ramat-Gan 52100, Israel, 7 pages, (Mar. 9, 1987).

(Continued)

*Primary Examiner*—Daniel L. Robinson
(74) *Attorney, Agent, or Firm*—Michael C. Staggs; Alan H. Thompson

(57) ABSTRACT

Near infrared imaging using elastic light scattering and tissue autofluorescence are explored for medical applications. The approach involves imaging using cross-polarized elastic light scattering and tissue autofluorescence in the Near Infra-Red (NIR) coupled with image processing and inter-image operations to differentiate human tissue components.

13 Claims, 5 Drawing Sheets

OTHER PUBLICATIONS

Zhang, G, et al., "Far-red and NIR Spectral Wing Emission from Tissues under 532 and 632 nm Photo-excitation," Lasers in the Life Sciences, vol. 9, pp. 1-16, (1999).

Alfano, R., et al., "Laser Induced Fluorescence Spectroscopy from Native Cancerous and Normal Tissue," IEEE Journal of Qantum Electronics, vol. QE-20, No. 12, pp. 1507-1511 (Dec. 1984).

Navone, N., et al, "Porphyrin biosynthesis in human breast cancer. Preliminary mimetic In vitro studies," Med. Sci. Res., 16, pp. 61-62, (1988).

Richards-Kortum, R., et al., "Spectroscopic Diagnosis of Colonic Dysplasia," Photochemistry and Photobiology, vol. 53, No. 6, pp. 777-786, (1991).

Demos, S., et al., "Subsurface Imaging Using the Spectral Polarization Difference Technique and NIR Illumination," Lawrence Livermore National Laboratory, UCRL-JC-131091 Preprint, 7 pages (Jan. 23, 1999).

Demos, S., et al., "Tissue imaging for cancer detection using NIR autofluorescence," Lawrence Livermore National Laboratory, 8 pages, (May 2002).

Schomacker, K., et al., "Ultraviolet Laser-Induced Fluorescence of Colonic Tissue: Basic Biology and Diagnostic Potential," Lasers in Surgery and Medicine, 12, pp. 63-78, (1992).

\* cited by examiner

NEAR-INFRARED SPECTROSCOPIC TISSUE IMAGING FOR MEDICAL APPLICATIONS

RELATED APPLICATION

This application is a division of U.S. application Ser. No. 10/190,231, filed Jul. 5, 2002 now U.S. Pat. No. 7,016,717, entitled "Near-Infrared Spectroscopic Tissue Imaging for Medical Applications."

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a medical diagnostic for the examination of tissue components. Specifically, the present invention relates to an apparatus and a method of polarized elastic light scattering, Near-infra-Red (NIR) autofluorescence emission combined with image processing and inter-image operations as an interrogation means for investigating tissue components for medical applications.

2. Description of Related Art

Diagnostic medical equipment typically includes time-consuming, bulky, expensive apparatus that often exposes human tissue components to potentially harmful radiation and or chemicals. Optical methods and systems for the identification of objects that possess different optical properties or abnormal compositions embedded in scattering media such as human tissue are desirable because such systems can be designed as compact, inexpensive, portable, and non-invasive spectral investigative tools. Optical spectroscopy, as one such optical method example, has been widely used to acquire fundamental knowledge about physical, chemical, and biological processes that occur in biomaterials. Most tissue spectroscopy research has employed UV to visible light sources from 250-nm to 600-nm. The main active fluorophores in this spectral region are tryptophan, collagen, elastin, NAD(P)H, flavins and prophyrins. The disadvantage of these wavelengths is their short photon penetration depth in tissues, which leads to extraction of information only from superficial tissue layers.

Accordingly, a need exists for optical diagnostic methods and systems to be utilized in a compact portable system to recover optical information with regard to human tissue and organ compositions.

SUMMARY OF THE INVENTION

Accordingly, the present invention is directed to an improved diagnostic imaging method for medical applications comprising the steps of: interrogating one or more tissue components with an electromagnetic source having predetermined wavelengths, detecting near infra-red scattered and autofluorescence emission from tissue components; and characterizing near-infrared autofluorescence coupled with optical scattering as an interrogation means for differentiating human tissue components.

Another aspect of the present invention provides a medical diagnostic method comprising the steps of: interrogating one or more tissue components using a substantially narrow-band electromagnetic source having one or more predetermined wavelengths of at least 500 nm, imaging tissue components with a device as a result of scattered and near-infrared electromagnetic emission from illuminated tissue components; and image processing recorded tissue component images by a computer having image processing software.

Still another aspect of the present invention is a diagnostic apparatus comprising: a substantially narrow-band electromagnetic radiation source; a device adapted to capture scattered and near-infrared emission from tissue components; and a means to characterize the captured radiation.

Accordingly, the present tissue imaging system and method provides a portable, cost effective, non-invasive arrangement, capable of directing substantially monochromatic electromagnetic radiation and capable of providing spectrally processed images in the much desired need for differentiating components in human and/or animal tissues.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1A:
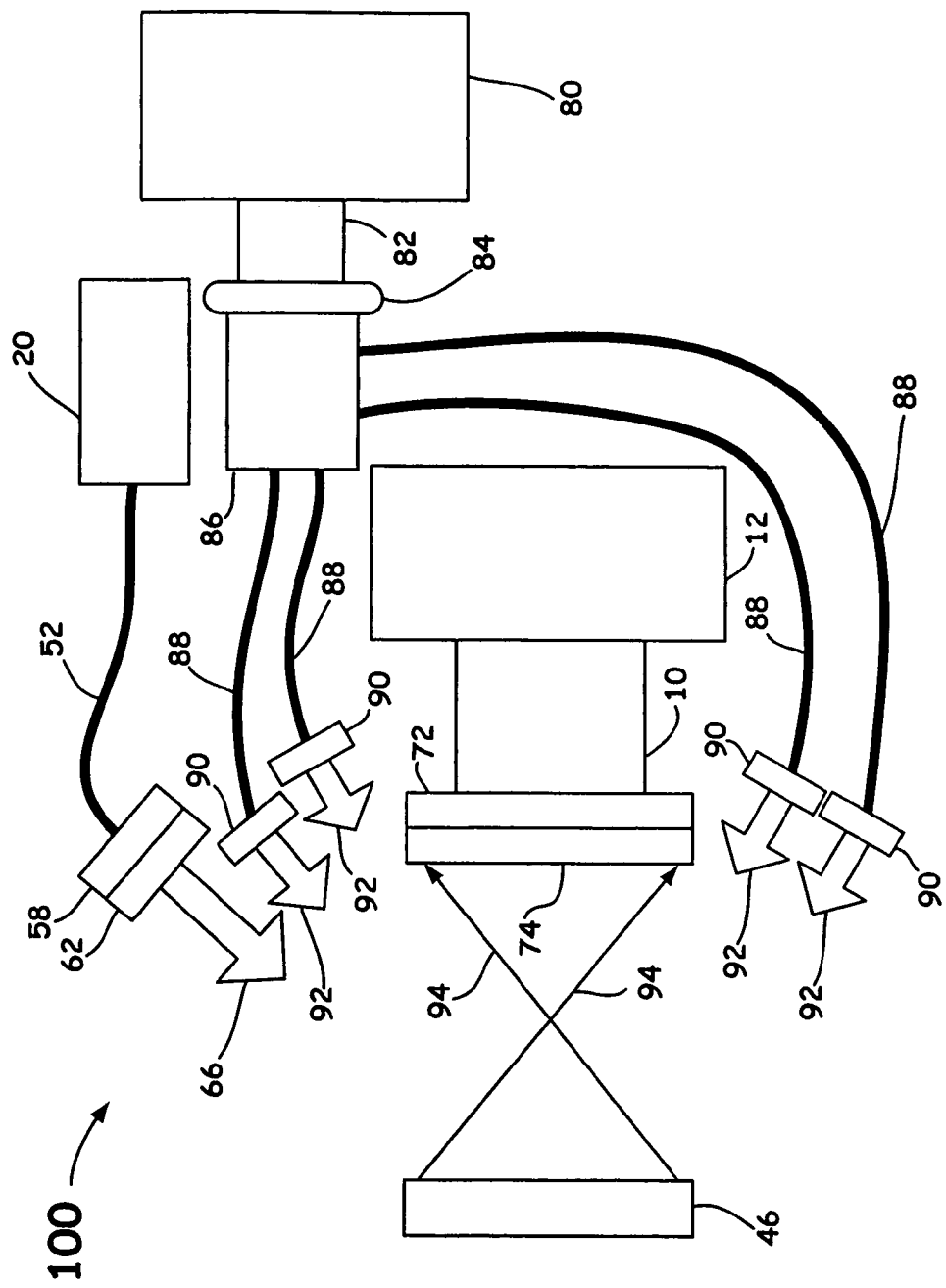
FIG. 1 is a simplified diagram of an exemplary medical tissue imaging apparatus incorporating elastic light scattering, fluorescence imaging, and image processing capabilities.

Referring now to the drawings, specific embodiments of the invention are shown. The detailed description of the specific embodiments, together with the general description of the invention, serves to explain the principles of the invention.

General Description

The present invention combines monochromatic laser sources, a broadband light source, optical filtering, a computer, optical imaging, and computer software capable of image analysis that includes inter-image operations. A useful feature of the present invention is that fresh surgical resections collected from patients may be measured in-vitro (e.g., in an artificial environment) and in-vivo (e.g., during medical biopsy or intervention procedures) immediately upon collection. In addition, the system has particular utility as a tissue component interrogation tool for human tissue specimens such as but not limited to kidney, uterine, bladder, breast, liver, adipose, abnormal (i.e., contrary to normal structure), normal, and veins and/or nerves from surrounding muscle tissue.

Accordingly, the present invention provides a non-invasive optical analysis means suitable for rapid, in-vitro or in-vivo differentiation of human tissue components.

Specific Description

Figure 1B:
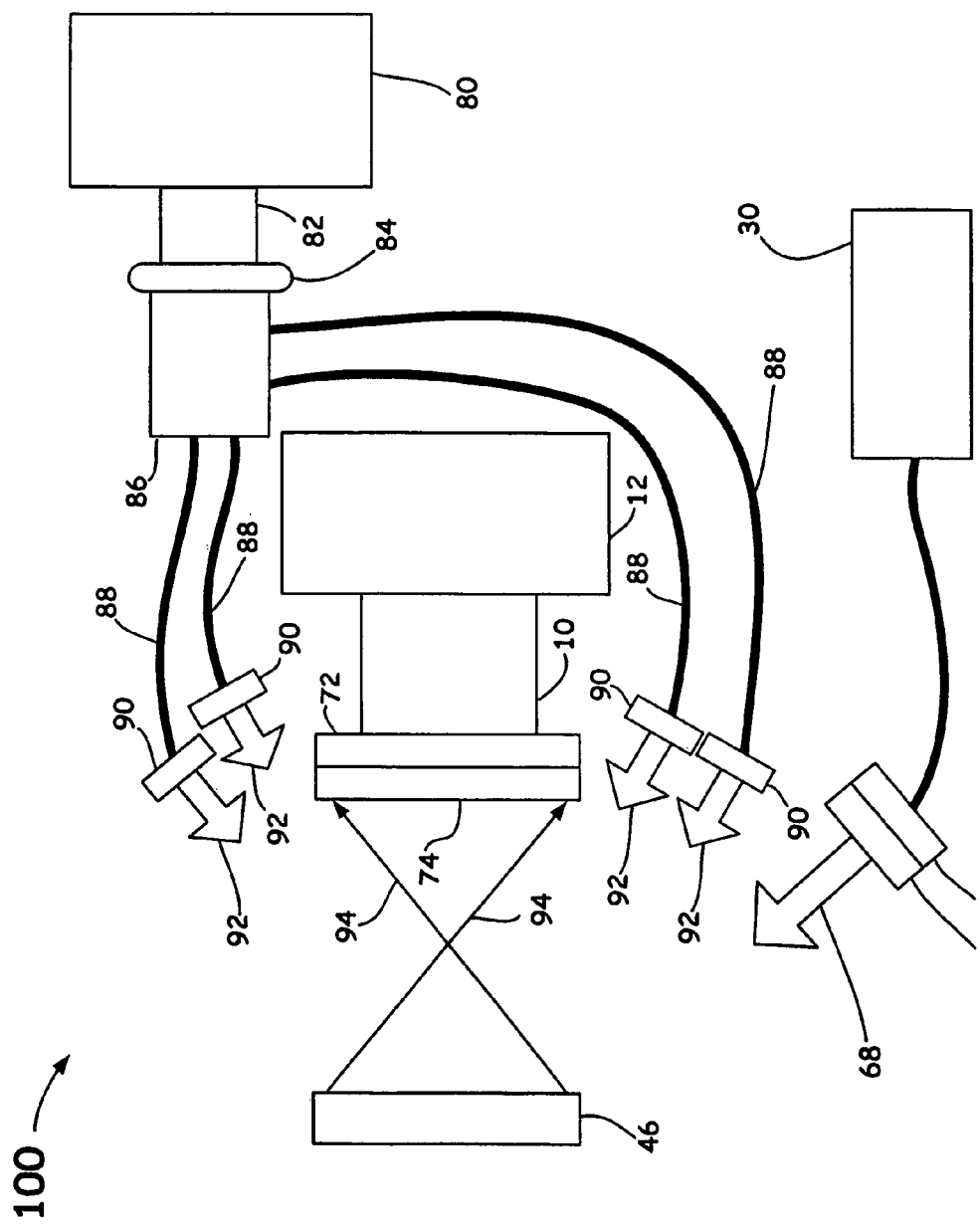

Turning now to the drawings, diagrams that illustrate exemplary embodiments of a system constructed in accordance with the present invention is shown in FIGS. 1A and 1B. The system, designated generally by the reference numeral 100, provides a method and apparatus for interrogating and characterizing human tissue components in a clinical environment from a specimen. System 100, designed as a portable, compact apparatus, includes the following basic components: a CPU with software for sample image processing (not shown); a lens system 10 for image collection; an image acquisition system 12; a substantially monochromatic 20 light source; an optical band-pass filters 62; an optical polarization filters 58; a sample holder (not shown); a white light source 80; and the remaining components (discussed below).

The sample image processing software (not shown) can be a commercially available product, by Roper Scientific Inc. However, any image analysis software capable of performing image processing with inter-image operations may be employed with the present invention to provide tissue component differentiation.

Lens system 10, for example a camera lens, is coupled to image acquisition system 12, such as, but not limited to, a liquid nitrogen cooled CCD camera, a two-dimensional array detector, an avalanche CCD photodetector, a photomultiplier or a photodiode capable of point by point scanning. However, any imaging device constructed to the design output parameters for image acquisition system 12 can also be employed in the present invention. Such exemplary image acquisition systems 12 capable of performing time-integrated images may be employed with the present invention to image illuminated tissue sample 46 housed in a kinematically (i.e., can be removed and rapidly repositioned with accuracy) mounted sample holder (not shown).

Monochromatic light sources 20 is a low power laser having an output power of at least 1 mW that operates at 632 nm. However, any laser source capable of providing a wavelength and intensity capable of differentiating tissue components may be employed with the present invention. White light source 80 provides a broadband of wavelengths for the scattering experiments. White light source 80 and monochromatic light source 20 are brought into the imaging compartment (not shown) by an optical means such as a plurality of large core optical fibers 52, and 88 (i.e., multimode fibers).

Monochromatic light source 20 is used for photoexcitation to provide NIR autoflurescence images, including a polarizer 58 and a narrow band-pass filter 62 positioned to ensure a predetermined narrow band of electromagnetic radiation with a predetermined polarization orientation to uniformly illuminate sample 46. White light source 80, to provide elastic light scattered images, additionally has one or more polarization filters 90 positioned to orient one or more illumination output beams 92 to a predetermined polarization orientation prior to uniformly illuminating a tissue specimen.

Sample 46 is illuminated with a set of one or more images, preferably seven, recorded for each sample. The objective is to employ hyperspectral (i.e., using various spectroscopic techniques and multiple wavelength and/or spectral bands) imaging to investigate the ability of polarized light in combination with native NIR autofluorescence to image and differentiate human tissue components. An exemplary useful benefit of the present invention is to image and differentiate human tissue components such as but not limited to cancerous growth from contiguous normal tissue or nerves and/or vascular structures from muscle.

The combined investigative approach method embodiment of polarized light scattering with NIR native tissue autofluorescence under long-wavelength laser excitation to reveal optical fingerprint characteristics for tissue components can be initiated by either of the following two methods of the present invention.

Autofluorescence

A related method for using autoflurescence emission (i.e., the spectral wing emission greater than 600 nm) to detect cancerous tissue is disclosed in Incorporated by reference Co-pending, Co-filed U.S. application Ser. No. 09/493,939 titled "Method And Apparatus For Examining A Tissue Using The Spectral Wing Emission therefrom Induced By Visible To Infrared Photoexcitation" by Alfano, et al., the disclosure is herein incorporated by reference in its entirety. NIR autofluorescence, as disclosed in the above referenced co-pending U.S. Application, is particularly useful for monitoring and/or imaging the porphyrin content in tissues. Porphyrins, effective at transferring electrons in sub-cellular organelles known as mitochondria are known to fluoresce in the visible light portion of the luminescence spectra. In addition, there is strong evidence that the heme-biosynthetic pathway, and therefore the production of porphyrins is disturbed in any new and abnormal growth such as cancer tissue. Thus, NIR autofluorescence of fluorophores, such as but not limited to porphyrins, provides one such exemplary medical diagnostic means of enhancing the contrast between normal and cancerous tissue components. However, the present invention provides a useful improvement thereof by incorporating autofluorescence images, image processing coupled with inter-image manipulations with elastic light scattering images discussed below to produce high contrast, high visibility images capable of differentiating substantially various human tissue components from a specimen such as but not limited to normal and tumor tissue.

Turning now to FIG. 1A, system 100 includes monochromatic light source 20 that transmits laser light through optical fiber 52. A preferred monochromatic light source 20 is a Helium-neon laser that operates at about 633 nm. However, any monochromatic laser light source operating at wavelengths from about 250 nm to about 1100 nm can be employed to provide NIR autofluorescence emission images for the present invention. Light source 20 is selected by a remote control pad (not shown) and directed by optical fiber 52 into an imaging compartment (not shown). Narrow-band filter 58 having an optical band-pass of at least 10 nm, and polarizer, 62 capable of producing linear, circular or elliptical polarization are positioned at the distal end of optical fiber 52 to ensure a degree of polarized monochromatic light beam 66 received from light source 20. The output of optical fiber 52 is constructed to provide beam 66 with a diverging property to substantially uniformly illuminate sample 46.

Referring now to FIG. 1B, system 100 shows an alternate embodiment that includes monochromatic light source 30, such as a Nd:YAG diode-pumped solid-state laser that operates at 532 nm, to transmit laser light through optical fiber 54. Light source 30 is selected by the remote control pad (not shown) and directed by optical fiber 54 into the imaging compartment (not shown). Narrow-band filter 60 having an optical band-pass of at least 10 nm, and polarizer, 64 capable of producing linear, circular or elliptical polarization are positioned at the distal end of optical fiber 54 to ensure a degree of polarized monochromatic light beam 68 received from light source 30. The output of optical fiber 54 is constructed to provide beam 68 with a diverging property to substantially uniformly illuminate sample 46.

Referring to FIG. 1A and FIG. 1B, Autofluorescence emission is generated from light sources 20 of FIG. 1A, or 30 of FIG. 1B, and then collected from tissue sample 46 in a back-scattering geometry, as generally shown by optical rays 94, by lens system 10 having one or more interchangeable camera lenses, preferably a 50-mm focal length camera lens. An analyzing polarizer 74 is positioned before lens system 10 on a translation stage such that parallel linear polarization, orthogonal cross-polarization, orthogonal elliptical polarization, same elliptical polarization, opposite circular polarization, or non-polarization analysis of the autofluorescence emission may be employed. A bandpass filter 72 is additionally positioned before lens system 10 to ensure a proper spectral band selection between about 650 nm and about 1500 nm for imaging. The autofluorescence emission is time gated for 0.1 or more seconds and recorded by image acquisition system 12, preferably a Princeton Instrument Model No. TE/CCD-512 liquid nitrogen cooled camera. The output of image acquisition system 12 is coupled to a computer (not shown), e.g., a laptop computer, and image processed by commercially available image processing software, such as Roper Scientific Winspec/32 and/or Winview/32 software, and displayed on, for example, a computer screen for human eye diagnosis or for image software analysis.

Elastic Light Scattering

The NIR polarized elastic light scattering method of the present invention to delineate differences in absorption and scattering in human tissue components allows an end-user to acquire clinical diagnostic deep-subsurface (e.g., at least 1 cm) images. An illumination wavelength, preferably greater than 500 nm from an electromagnetic radiation source is utilized to provide mean photon penetration depth larger than 1 mm. Linear cross-polarization and spectral analysis of the scattered photons substantially removes the photon information from the orthogonal illumination polarization resulting from the surface and allows substantially all of the scattered photons from the subsurface tissue to be imaged.

In addition, a spectral polarization difference technique (SPDI) and NIR illumination related method embodiment is utilized in the present invention and is disclosed in incorporated by reference, U.S. application Ser. No. 5,847,394, titled "Imaging of objects based upon the polarization or depolarization of light," by Alfano, et al., the disclosure which is herein incorporated by reference in its entirety. With SPDI, different illumination wavelengths are utilized to record images having a differential mean photon penetration depth. Thus, a smaller differential in the illumination wavelengths provides narrower differential depth zones while a larger difference in two exemplary illuminating wavelengths gives rise to a wider depth zone. Cross-polarization and normalization analysis coupled with inter-image operations such as but not limited to subtraction between one or more illuminating wavelengths provide information as to the tissue structure between the penetration depths of the one or more respective probe illumination wavelengths. However, the present invention provides a useful improvement thereof, as similarly discussed herein before, by incorporating inter-image operations of autofluorescence images and light scattering, such as single wavelength cross-polarized light scattered images, to provide higher visibility and contrast information from images for humans tissue component differentiation.

Accordingly, the present invention utilizes NIR autofluorescence, NIR light scattering, inter-image operations between individual methods, (preferably inter-image operations incorporating both autofluorescence and light scattering), to provide differential tissue component information within one or more exemplary images.

Turning again to FIG. 1A or FIG. 1B, a broad-band, i.e., its electromagnetic spectrum covers the visible, (e.g., 0.4 μm to 0.7 μm), and a substantial amount of the invisible, (e.g., 0.7 μm to 2.0 μm), white light source 80 is selected by the remote pad (not shown) to transmit up to 100 watts of white light to coupled optical fiber bundle 82. Fiber bundle 82 has its distal end coupled to a tunable filter (not shown) or a filter wheel 84 that is remotely controlled by a filter wheel remote pad (not shown) for insertion of a predetermined optical filter (not shown). Such a predetermined narrow-band (e.g., 40 nm) interference filter in the visible or invisible between about 700-nm and about 1000-nm spectral range can thus be rapidly positioned at the output distal end of fiber bundle 82. However, any type of band-pass filter means, for example broad spectral band filters or long-pass interference filters can be employed in practice of the invention.

A manifold 86 is coupled to an optical delivery means such as one or more large core optical fibers 88, preferably four. Manifold 86 is additionally coupled to filter wheel 84 to receive and direct the selected wavelength band through optical fibers 88 in order to substantially uniformly illuminate sample 46. One or more linear polarizers 90 are constructed at the output of one or more optical fibers 88 to ensure a degree of linear polarization of one or more scattering diverging illumination output beams 92 having predetermined selected wavelength bands.

The elastically scattered light is then collected from tissue sample 46 in a back-scattering geometry, as generally shown by optical rays 94, by lens system 10 similar to the autofluorescence measurements discussed above. Analyzing polarizer 74 is positioned on a translation stage such that parallel polarization, cross-polarization or non-polarization analysis of the elastic light scattering may be employed. Image acquisition system 12 is time gated for 0.1 or more seconds and one or more images as a result of the elastic light scattering from the sample is recorded. The output of image acquisition system 12 is coupled to a computer (not shown), e.g., a laptop computer, image processed, and displayed on, for example, one or more computer screens for human eye diagnosis or for image software analysis as previously discussed.

An exemplary prototype was constructed and positioned in a lab space located at the UC Davis Medical Center in Sacramento, Calif. The following autofluorescence emission and elastic light scattering images illustrating adipose, cancerous and contiguous normal human tissue, obtained from fresh surgical resections from more than 60 patients are used to only illustrate some of the novel imaging capabilities of the present invention.

Figure 2A:
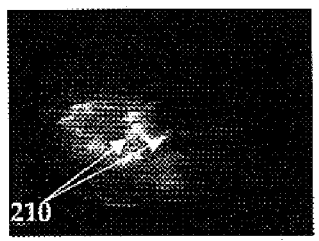
FIG. 2 shows a series of breast tissue images collected by the present invention.
Figure 2C:
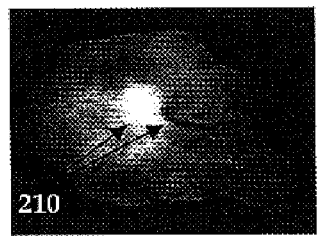
Figure 2E:
Figure 2B:
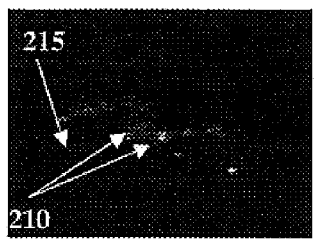
Figure 2D:
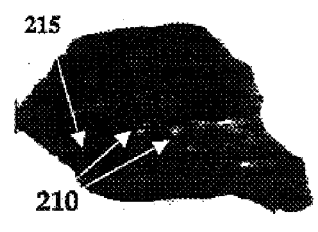
Figure 2F:
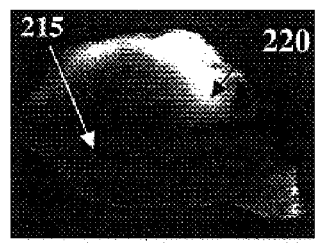

FIG. 2 illustrates a capability of the present invention with a set of images of an approximately 4-cm×3-cm human breast tissue specimen 204 with multifocal high grade ductal carcinoma 210 shown in FIG. 2d, surrounded by fibrous supporting tissue 215 with an adjacent area of fatty 220 (i.e., adipose) infiltration as shown in FIG. 2f. FIGS. 2a and 2b show Autofluorescence images in the 700-nm and 1000-nm spectral region under a 532-nm and a 633-nm substantially monochromatic illumination, respectively. FIG. 2c shows a light scattering image of specimen 204 under 700-nm illumination. FIG. 2d shows a novel feature of the present invention wherein a ratio of the Autofluorescence image of FIG. 2b, divided by the light scattering image of FIG. 2c, improves visibility and contrast of a pair of higher emission 1-mm diameter ductal carcinoma lesions 210 as determined by histopathological (i.e., microscopic tissue disease) assessment (i.e., hematoxylin-eosin stain). In addition, the ratio image provides better delineation of the tumor margins. This effect is also demonstrated in the examples shown in succeeding FIGS. 3 through 5. Furthermore, FIG. 2e shows an inter-image ratio of a cross-polarized light scattering 1000 nm band-pass image (not shown) divided by the cross-polarized light scattering 700 nm band-pass image of FIG. 2c. FIG. 2f shows an inter-image ratio of cross-polarized light scattering 700 nm band-pass image of FIG. 2c divided by the Autofluorescence image after 532 nm illumination of FIG. 2a.

From the images of the specimen shown in FIG. 2, only the NIR fluorescence image under 632.8-nm excitation FIG. 2b and the ratio image of FIG. 2d show a correlation with the assessment of lesions 210. The integrated NIR emission intensity arising from these cancerous parts of the sample is higher than surrounding tissue 215 of FIGS. 2b, 2d, and 2f, by a factor of about 1.5 in FIG. 2b and a factor of about 1.6 in FIG. 2d. FIG. 2e and FIG. 2f show the presence of adipose tissue 220 with a higher average intensity of adipose tissue component 220 compared to the surrounding connective tissue 215 of FIG. 2e and FIG. 2f of about 0.25 and 2.5 for the image shown in FIG. 2e and FIG. 2f, respectively. The ratio images of FIG. 2d and FIG. 2f reveal high contrast and increased visibility of different tissue components (i.e., lesions 210 of FIG. 2d and adipose 220 tissue of FIG. 2f, respectively) while subjecting specimen 204 to different illumination wavelengths and by different inter-image operations. Thus, the present invention can be advantageous in increasing the visibility of various tissue components in a specimen by varying system parameters (i.e., illumination wavelength, spectral band-pass region, inter-image operations, etc.).

FIG. 3 shows a set of images obtained from two liver specimens. FIGS. 3a, 3b, and 3c, show a histologic section of a specimen 206, taken from a benign growth as determined by clinical assessment. FIGS. 3d, 3e, and 3f, show a histologic section of a specimen 208 of a well-circumscribed 0.8×0.5-cm nodule. The histologic features of the nodule, as determined by clinical assessment, are those of a hepatoblastoma (i.e., a tumor of the liver). FIGS. 3a and 3d are NIR autofluorescence images recorded under 632-nm illumination, respectively. FIGS. 3b and 3e are NIR cross-polarized light scattering images recorded under 700-nm illumination respectively. FIGS. 3c and 3f are the resultant ratio images of the autofluorescence images FIGS. 3a and 3d over light scattering images 3b and 3e, respectively. Benign tumor 310 is visible in specimen 206 of image 3c. The digitized intensity in the area of the benign tumor 310 is higher between about 0.20 when compared to that of the adjacent normal liver tissue 315. However, organ composition, depth of tissue components, and illumination and inter-image operations, may vary the digitized intensity information so as to best visualize specific tissue components.

Figure 3A:
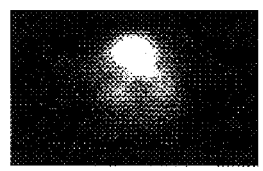
FIG. 3 shows a series of malignant and benign tumor images from a liver specimen collected by the present invention.
Figure 3B:
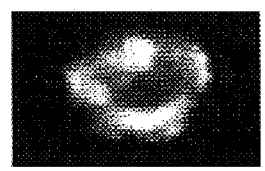
Figure 3C:
Figure 3D:
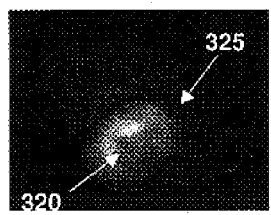
Figure 3E:
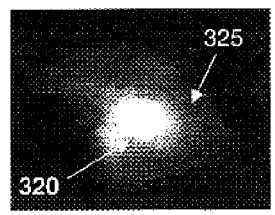
Figure 3F:
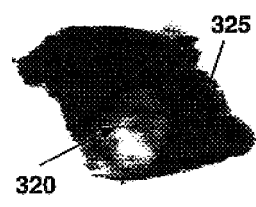

It is noted however, that cancer nodule 320, in specimen 208 of FIGS. 3d, 3e, and 3f, is shown as an even brighter in intensity feature with respect to a surrounding normal tissue 325. More specifically, this intensity difference between tissue components 320, and adjacent normal tissue 325 is further increased in NIR autofluorescence image FIG. 3d under 632.8-nm excitation by a factor of about 0.65. In FIG. 3e (cross-polarized light scattering image under 700-nm illumination) the digitized intensity in the area of the cancer nodule 320 is higher by a factor of about 0.15 when compared to that of the adjacent normal liver tissue 325. However, the highest contrast accompanied by best visualization of tissue margins of cancer nodule 320 is in the ratio image shown in FIG. 3f, wherein an overall intensity difference between cancer nodule 320 and adjacent normal tissue 325 is a factor of up to about 0.90.

Figure 4A:
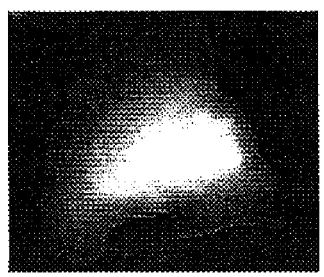
FIG. 4 shows a series of uterine images collected by the present invention.
Figure 4B:
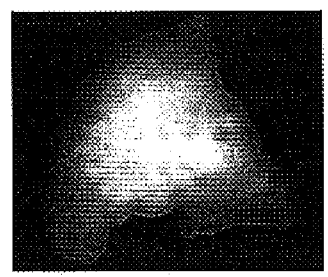
Figure 4C:
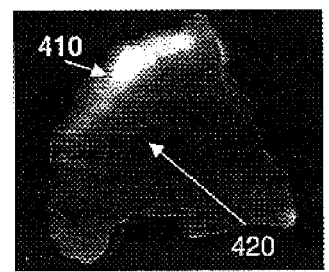
Figure 5A:
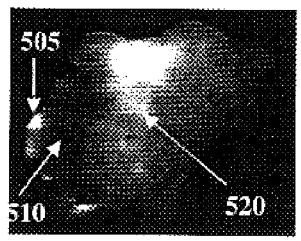
FIG. 5 shows a series of bladder images collected by the present invention.
Figure 5B:
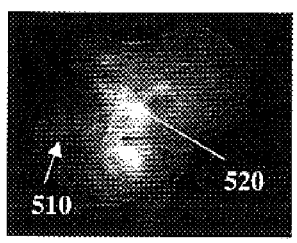

FIGS. 4a, 4b, and 4c, and FIGS. 5a, 5b, and 5c show images of the method of the present invention in delineating cancerous uterine and bladder tissue from adjacent normal tissue, respectively. FIGS. 4a and 5a show NIR autofluorescence images of the uterine and bladder organs under 632-nm illumination respectively while FIGS. 4b and 5b show NIR cross-polarized images of the respective organs under 700-nm illumination.

For the uterine specimen, FIG. 4c (i.e., the ratio of NIR cross-polarized image under 700-nm illumination of FIG. 4b over NIR autpofluorescence image under 632-nm illumination of FIG. 4a), shows a contrast ratio that clearly differentiates cancerous uterine tissue 410 from surrounding tissue, including normal tissue 420. Specifically, FIG. 4c shows a contrast ratio of digitized counts of cancerous tissue 410 from adjacent normal tissue 420 by a factor of at least 0.65. However, as discussed herein before, tissue depth, composition, etc., results in different contrast ratios but with the same qualitative visual assessment.

Figure 5C:
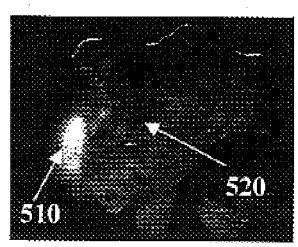

FIG. 5c (i.e., the ratio of NIR cross-polarized image under 700-nm illumination FIG. 5b over NIR autpofluorescence image under 632-nm illumination FIG. 5a) shows a high visibility, high contrast bladder cancerous tissue 510 from surrounding normal bladder tissue 520 similar to the case for uterine tissue shown in FIG. 4. FIG. 5a shows necrotic tissue 505 (cells that have died as a result of cancerous growth) as a high intensity region. Moreover, FIG. 5a (NIR autofluorescence image under 632-nm illumination) and FIG. 5b (NIR cross-polarized image under 700-nm illumination) also show cancerous tissue 510 as a dark feature that is about 0.40 less in digitized intensity with respect to the surrounding lighter featured normal bladder tissue 520. However, better contrast and better visibility is still the image shown in FIG. 5c as compared in FIG. 5a and FIG. 5b separately.

The present invention thus combines advantageous methods for tissue component differentiation. The first method examines polarized light scattering spectral imaging. The images attained using elastic light scattering delineate differences in absorption and scattering between tissue components.

Another advantageous method of the present invention involves imaging of various tissue types using the NIR emitted light under, for example, 632.8-nm and 532-nm excitation. The images attained using this method are useful for monitoring and/or imaging endogenous fluorescing agents, such as porphyrins, which is useful for the detection of neoplastic (i.e., diseased) tissue formation. In addition, NIR autofluorescence is further enhanced by utilizing excitation at different wavelengths. For example the 1-mm tumor lesions in the breast specimen depicted in FIG. 2c are visible in the NIR autofluorescence images under 632.8-nm excitation but not under 532-nm excitation. Therefore, different illumination wavelengths provided by the present invention can provide insight into different fluorophores that are indicative of neoplastic human or animal tissue. Moreover, inter-mage operations of the present invention, such as but not limited to light scattering over NIR autofluorescence images, has particular utility for high contrast, high visibility images for tissue component differentiation.

Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The invention claimed is:

1. A diagnostic apparatus, comprising:
a substantially narrow-band electromagnetic radiation source directed to illuminate one or more tissue components,
a device adapted to detect and record an analyzed degree of polarization near-infra red scattered electromagnetic radiation and a near infrared autofluorescence emission resulting from said illuminated tissue components; and
means to characterize said tissue components, further comprising inter-image operations on said detected scattered radiation and said near infrared autofluorescence emission to enhance image contrast and visibility of said tissue components.

2. The apparatus of claim 1, wherein said apparatus is substantially compact and substantially lightweight to be used for an in-vivo application.

3. The apparatus of claim 1, wherein said means to characterize said tissue components further comprises a computer having image processing software and one or more computer display screens.

4. The apparatus of claim 1, wherein said source comprises one or more lasers having wavelengths greater than 500 nm.

5. The apparatus of claim 1, wherein said source further comprises one or more commercially available compact lasers.

6. The apparatus of claim 1, wherein said source further comprises a diode or one or more substantially monochromatic light sources.

7. The apparatus of claim 1, wherein said source is a broad band lamp designed to transmit predetermined filtered wavelengths between about 600 nm and about 1500 nm through an optical means to substantially uniformly illuminate said tissue sample.

8. The apparatus of claim 1, wherein said produced scattered electromagnetic radiation is predetermined from optical band-pass filters comprising between about 10 and about 40 nm of bandwidth.

9. The apparatus of claim 1, wherein said source capable of one or more substantially monochromatic wavelengths and said camera are remotely controlled.

10. The apparatus of claim 1, wherein one or more optical polarizers can be adapted to produce a degree of polarization on an output of said source and wherein said analyzed degree of polarization comprises one or more polarizers adapted to analyze said scattered electromagnetic radiation and said near infra-red emission received from said tissue components.

11. The apparatus of claim 1, wherein said tissue components are positioned on a stage capable of being manually moved to a desired location and capable of being remotely controlled from said computer having a software program designed to move said stage.

12. The apparatus of claim 1, wherein said recorded near-infrared emission is between about 600 nm and about 1500 nm.

13. The apparatus of claim 1, wherein said device is selected from a liquid nitrogen cooled CCD camera, a two-dimensional array detector, an avalanche CCD photodetector, a photomultiplier and a photodiode capable of point by point scanning.

* * * * *